United States Patent
Destoumieux et al.

(10) Patent No.: US 6,642,203 B1
(45) Date of Patent: Nov. 4, 2003

(54) CRUSTACEAN ANTIMICROBIAL PEPTIDES

(75) Inventors: Delphine Destoumieux, Montpellier (FR); Evelyne Bachere, Clapiers (FR); Philippe Bulet, Vendenheim (FR)

(73) Assignees: Institut Francais de Recherche pour l'Exploitation de la Mer, Issy les Moulineaux (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/463,125

(22) PCT Filed: Jul. 20, 1998

(86) PCT No.: PCT/FR98/01583

§ 371 (c)(1),
(2), (4) Date: Apr. 12, 2000

(87) PCT Pub. No.: WO99/05270

PCT Pub. Date: Feb. 4, 1999

(30) Foreign Application Priority Data

Jul. 21, 1997 (FR) .............................................. 97 09214

(51) Int. Cl.[7] ..................... A61K 38/17; C07K 14/435; C12N 15/12
(52) U.S. Cl. ........................ 514/12; 530/300; 435/69.1; 435/252.8; 435/254.1; 435/320.1; 435/325; 536/23.1
(58) Field of Search .......................... 530/300; 514/12; 435/254.1, 69.1, 252.8, 320.1, 325; 536/23.1

(56) References Cited

PUBLICATIONS

Destoumieux, D. et al., "Penaeidins, a New Family of Antimicrobial Peptides Isolated from the Shrimp *Penaeus vannamei* (Decapoda)," J Biol Chem, 272(45):28398–28406, Nov. 7, 1997.

Ehret–Sabatier, L. et al., "Characterization of Novel Cysteine–rich Antimicrobial Peptides from Scorpion Blood," J Biol Chem, 271(47):29537–29544, Nov. 22, 1996.

Kuhn, R. et al., *Drosophila melanogaster* Male Specific Sperm Protein MST84DC, Accession No. Q01644, Swissprot database, Jul. 1993.

Schnapp, D. et al., "Purification and characterization of a proline–rich antibacterial peptide, with sequence similarity to bactenecin–7, from the haemocytes of the shore crab, *Carcinus maenas*," Eur J Biochem, 240:532–539, 1996.

*Primary Examiner*—Christopher S. F. Low
*Assistant Examiner*—Chih-Min Kam
(74) *Attorney, Agent, or Firm*—Morgan Lewis & Bockius LLP

(57) ABSTRACT

The invention concerns antimicrobial peptides obtained from penaeid prawns having the following characteristics: a molecular mass of about 5 to 7 kDa; a pHi not less than 9; an N-terminal portion comprising a region (A) of about 15 to 25 amino acids rich in proline; and a C-terminal portion comprising a region (B) of about 20 to 30 amino acids and containing 6 cysteine residues forming three intramolecular disulfide bonds. The invention also concerns the nucleic acid sequences coding for said peptides and enabling their production by genetic engineering.

Figure 4:
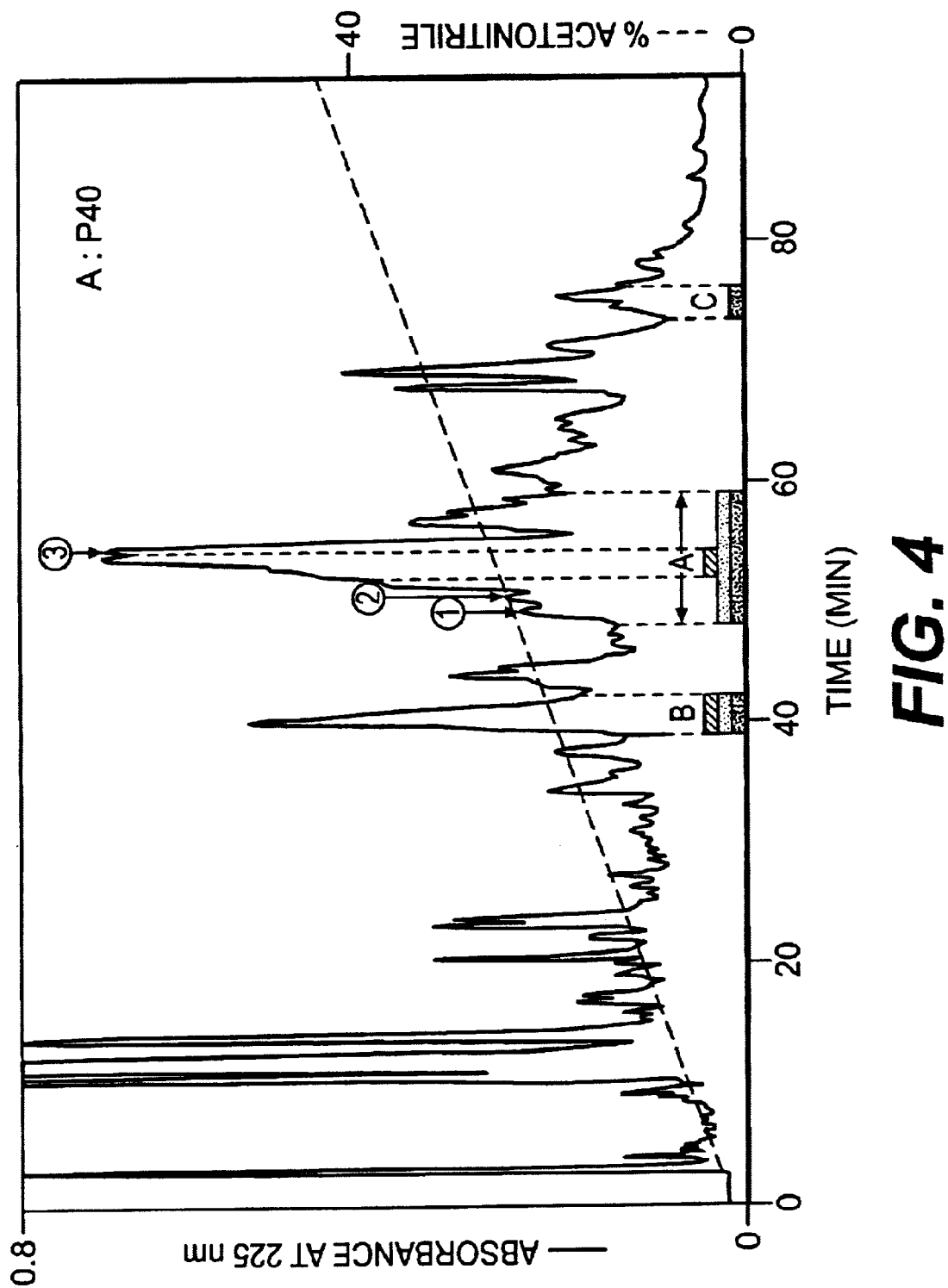

9 Claims, 5 Drawing Sheets a) YRGGYTGPIPRPPPIGRPPLRLVVCACYRLSVSDARNCCIKFGSCCHLVK b) YRGGYTGPIPRPPPIGRPPFRPVCNACYRLSVSDARNCCIKFGSCCHLVK* c) pEVYKGGYTRPIPRPPPFVRPLPGGPIGPYNGCPVSCRGISFSQARSCCSRLGRCCHVGKGYS* d) YRGGYTGPIPRPPPIGRPPLR-----LVVC--ACYRLSVSDARNCCIKFGSCCHLVK
YRGGYTGPIPRPPPIGRPPFR------PVC-NACYRLSVSDARNCCIKFGSCCHLVK*
pEVYKGGYTRPIPRPPPFVRPLPGGPIGPYNGCPVSCRGISFSQARSCCSRLGRCCHVGKGYS*

FIG. 1

```
                                                                                                    Met Arg Leu Val Val
  1  AAT TCG GCA CGA GCT CCC TCT AGC CTC ACC TGC AGA GAC CGA CGC TCC GAG CCC GGG TTC CCT CCT GCG TCC GCC ATG CGC CTC GTG GTC
                                                                                                                         14
                                                                     ←——1
        Cys Leu Phe Leu Ala Ser Phe Ala Leu Val Cys Gln Gly Glu Ala Tyr Arg Gly Gly Tyr Thr Gly Pro Ile Pro Arg Pro Pro Pro
 91     TGC CTG TTC CTC TTG GCC TCC TTC GCC CTG GTC TGC CAA GGC GAA GCG TAC AGG GGC GGT TAC ACA GGC CCG ATA CCC AGG CCA CCA CCC
        15                                                                                                                44
        Ile Gly Arg Pro Phe Arg Pro Val Cys Asn Ala Cys Tyr Arg Leu Ser Val Ser Asp Ala Arg Asn Cys Ile Lys Phe Gly Ser
181     ATT GGA AGA CCG TTC AGA CCT GTT TGC AAT GCA TGC TAC AGA CTT TCC GTC TCA GAT GCT CGC AAT TGC ATC AAG TTC GGA AGC
        45
        Cys Cys His Leu Val Lys Gly   *
271     TGT TGT CAC TTA GTA AAA GGA TAA AGA AAT TGA CGG AGA AGA CAA TGG ATC TCT CGC TTG ACA ACT TGT TAA TTA ATA CTC ATA TGT GAA
        51
361     GAG ATT GCA ACC CTG ATT TGT GTC AAG GAT GTG CTT AAG CAT GTG ATT TCG GGT ATT TGC ATG CAT CCG TTC TTC CAT GAA AGA TGT ATG AAG GAA AGT
451     GCA TGT GTG TAA GTA TAT GTG CTT ACA GGT ATT TAG GAT CTT CCG TGT ATT CAG TGT TGG GTT CGG TGT CAA CAC ACG AGG AAG AGA
541     ATA TTT GCC ACT ACT TGC CAT TTA TTT CAG TTT CTG TAA ATC TGT GAG AGG TTG ACA GAT CTC TCT TTT ACA AAT AAA TTT
631     GAT ATC TGT GAA AAA AAA AAA AAA A
```

FIG. 2

A

```
1    A ATT CGG CAC GAG TCG AGC CTC ACC TGC AGA GAC CGA CGC TCC CCT CCT GCG TTC CCT GGG GGT TAC ACG CGC CCG ATA CCC AGG CCA CCA CCC TTC
                                                                    Met Arg Leu Val Val Cys
                                                                                          17
                                                                    Leu Val Phe Leu Ala Ser Phe Leu Ala Leu Val Cys Gln Val Tyr Lys Gly Gly Tyr Thr Arg Pro Ile Pro Arg Pro Pro Phe
89   CTG GTC GTC TGC CTT GTC TTC CTC GCC TCC TTC CTG GCC CTG GTC TGC CAA GGC GGT TAC ACG CGC CCG ATA CCC AGG CCA CCA CCC TTC
18                                                                                                                         47
     Val Arg Pro Gly Gly Pro Ile Gly Pro Tyr Asn Gly Cys Pro Val Ser Cys Arg Gly Ile Ser Phe Ser Gln Ala Arg Ser Cys
179  GTG AGA CCT TTG CCA GGA GGG CCT ATT GGT CCA TAC AAC GGT TGC CCT GTC TCA TGC CGG GGA ATT TCC TTC TCA CAA GCG CGT TCT TGC
48                                                                                                                          63
     Cys Ser Arg Leu Gly Arg Cys Cys His Val Gly Lys Gly Tyr Ser Gly  *
269  TGC TCC CGG CTT GGG CGT TGC TGC CAC GTG GGA AAG GGA TAT TCC GGT TGA TGG AGA ACA CGA TGA AAA CCT CGC TTG ACA ACC TGT TGA
359  TTG ATA CTT GTA TGT GAA GAG ACT GTT TTT TAA GAC TTT CAC CGT TTG CGC CAT TGC CCG AGG TGG GTG TGT GAT CTG AGT ATG AAA AAA AAA
449  GTT ATT TGA CCC AGC AGG TGG CGC CAT TGC CCG AGG TGG GTG TGT GAT CTG AGT ATG AAA AAA AAA
539  CAA CGT CCC AGC AGG TGG CGC CAT TGC CCG AGG TGG GTG TGT GAT CTG AGT ATG AAA AAA AAA
629  AGT ATG GAT CTG AGT ATG AAA AAA AAA
719  AAA AAA AAA AAA AAA
```

B

```
P3-a    MRLVVCLVFLASFALVCQGQVYKGGYTRP PR PPFVRP PGGPIGPYNGCPVSCRGISFSQARSCCSRLGRCCHVGKGYSG
P3-b    MRLVVCLVFLASFALVCQGQVYKGGYTRP PR PPFVRP PGGPIGPYNGCPVSCRGISFSQARSCCSRLGRCCHVGKGYSG
P3-c    MRLVVCLVFLASFALVCQGQVYKGGYTRP PR  PPFVRP PGGPIGPYNGCPVSCRGISFSQARSCCSRLGRCCHVGKGYSG
```

FIG. 3

SEQUENCE LISTING

<160> NUMBER OF SEQ ID NOS: 24

<210> SEQ ID NO 1
<211> LENGTH: 658
<212> TYPE: DNA
<213> ORGANISM: Penaeus vannamei
<220> FEATURE:
<221> NAME/KEY: CDS
<222> LOCATION: (76)..(294)
<220> FEATURE:
<221> NAME/KEY: mat_peptide
<222> LOCATION: (139)..(294)

<400> SEQUENCE: 1

```
aattcggcac gagctccctc tagcctcacc tgcagagacc gacgctccga gcccgggttc       60
cctcctgcgt ccgcc atg cgc ctc gtg gtc tgc ctg gtc ttc ttg gcc tcc     111
              Met Arg Leu Val Val Cys Leu Val Phe Leu Ala Ser
                  -20                 -15                 -10 ttc gcc ctg gtc tgc caa ggc gaa gcg tac agg ggc ggt tac aca ggc       159
Phe Ala Leu Val Cys Gln Gly Glu Ala Tyr Arg Gly Gly Tyr Thr Gly
            -5                   -1   1                   5 ccg ata ccc agg cca cca ccc att gga aga cca ccg ttc aga cct gtt       207
Pro Ile Pro Arg Pro Pro Pro Ile Gly Arg Pro Pro Phe Arg Pro Val
         10                  15                  20 tgc aat gca tgc tac aga ctt tcc gtc tca gat gct cgc aat tgc tgc       255
Cys Asn Ala Cys Tyr Arg Leu Ser Val Ser Asp Ala Arg Asn Cys Cys
     25                  30                  35 atc aag ttc gga agc tgt tgt cac tta gta aaa gga taa agaaattgac        304
Ile Lys Phe Gly Ser Cys Cys His Leu Val Lys Gly
 40                  45                  50 ggagaagaca atggaaacct ggcttgacaa cttgttaatt aatactcata tgtgaagaga     364
ttgcaaccct gatttgtgtc aaggatgtgg gtatttcgtc tatccatcgc taaagattct     424
tccatgaatg tatgatgaag gaaagtgcat gtgtgtaagt atgtatgtat gtgcttacag     484
gtatttgttg cattaagtgt ccgtgtattt aggatctgca acacacgagg aagagaatat     544
ttgccacttg ccatttattt cagtttctgt aagtgtggat ctgtgagagg ttggtgttga     604
cagatctctc ttttacaaat aaatttgata tctgtgaaaa aaaaaaaaa aaaa            658
```

<210> SEQ ID NO 2
<211> LENGTH: 72
<212> TYPE: PRT
<213> ORGANISM: Penaeus vannamei

<400> SEQUENCE: 2

```
Met Arg Leu Val Val Cys Leu Val Phe Leu Ala Ser Phe Ala Leu Val
 1               5                  10                  15

Cys Gln Gly Glu Ala Tyr Arg Gly Gly Tyr Thr Gly Pro Ile Pro Arg
             20                  25                  30
```

```
Pro Pro Pro Ile Gly Arg Pro Pro Phe Arg Pro Val Cys Asn Ala Cys
        35                  40                  45

Tyr Arg Leu Ser Val Ser Asp Ala Arg Asn Cys Cys Ile Lys Phe Gly
 50                  55                  60

Ser Cys Cys His Leu Val Lys Gly
 65              70

<210> SEQ ID NO 3
<211> LENGTH: 736
<212> TYPE: DNA
<213> ORGANISM: Penaeus vannamei
<220> FEATURE:
<221> NAME/KEY: CDS
<222> LOCATION: (71)..(319)
<220> FEATURE:
<221> NAME/KEY: mat_peptide
<222> LOCATION: (128)..(319)

<400> SEQUENCE: 3
aattcggcac gagtcgagcc tcacctgcag agaccgacgc tccgagcccg ggttccctcc      60
tgcgtccgcc atg cgc ctc gtg gtc tgc ctg gtc ttc ttg gcc tcc ttc      109
            Met Arg Leu Val Val Cys Leu Val Phe Leu Ala Ser Phe
                        -15                 -10
gcc ctg gtc tgc caa ggc caa gtg tac aag ggc ggt tac acg cgc ccg      157
Ala Leu Val Cys Gln Gly Gln Val Tyr Lys Gly Gly Tyr Thr Arg Pro
        -5          -1  1               5                   10
ata ccc agg cca cca ccc ttc gtg aga cct ttg cca gga ggg cct att      205
Ile Pro Arg Pro Pro Pro Phe Val Arg Pro Leu Pro Gly Gly Pro Ile
                15                  20                  25
ggt cca tac aac ggt tgc cct gtc tca tgc cgg gga att tcc ttc tca      253
Gly Pro Tyr Asn Gly Cys Pro Val Ser Cys Arg Gly Ile Ser Phe Ser
            30                  35                  40
caa gcg cgt tct tgc tgc tcc cgg tta ggg cgt tgc tgt cac gtg gga      301
Gln Ala Arg Ser Cys Cys Ser Arg Leu Gly Arg Cys Cys His Val Gly
                45                  50                  55
aag gga tat tcc ggt tga tggagaacac gatgaaaacc tcgcttgaca             349
Lys Gly Tyr Ser Gly
        60 acctgttgat tgatacttgt atgtgaagag actgtgatcc tgattttgca ctgtgttttc    409 tcgttcaata ttcttactct ggcttgtgga atggatgtag ttatttgacc ctatgttttt    469 ttttaagact tttccatgaa tgcacgatga atgaaagctt gcgtgatatg aatgagtgca    529 tccacttttc aacgtcccag caggtggcgc cgtattcatg atttgtgaca cacgaggaag    589 taaatccatg ccatctgcct ttcgttgtaa ttttagtga gtatggatct gtgtgtgggt    649 gattttaca aatctctcaa aggactttta gaaatgttac tcctttacaa ataaaattgg    709 tatcttgaaa aaaaaaaaaa aaaaaaa                                       736

<210> SEQ ID NO 4
<211> LENGTH: 82
<212> TYPE: PRT
<213> ORGANISM: Penaeus vannamei

<400> SEQUENCE: 4

Met Arg Leu Val Val Cys Leu Val Phe Leu Ala Ser Phe Ala Leu Val
 1               5                  10                  15

Cys Gln Gly Gln Val Tyr Lys Gly Gly Tyr Thr Arg Pro Ile Pro Arg
             20                  25                  30

Pro Pro Pro Phe Val Arg Pro Leu Pro Gly Gly Pro Ile Gly Pro Tyr
         35                  40                  45

Asn Gly Cys Pro Val Ser Cys Arg Gly Ile Ser Phe Ser Gln Ala Arg
     50                  55                  60
```

Ser Cys Cys Ser Arg Leu Gly Arg Cys Cys His Val Gly Lys Gly Tyr
65                  70                  75                  80

Ser Gly

<210> SEQ ID NO 5
<211> LENGTH: 50
<212> TYPE: PRT
<213> ORGANISM: Penaeus vannamei

<400> SEQUENCE: 5

Tyr Arg Gly Gly Tyr Thr Gly Pro Ile Pro Arg Pro Pro Pro Ile Gly
1               5                   10                  15

Arg Pro Pro Leu Arg Leu Val Val Cys Ala Cys Tyr Arg Leu Ser Val
            20                  25                  30

Ser Asp Ala Arg Asn Cys Cys Ile Lys Phe Gly Ser Cys Cys His Leu
        35                  40                  45

Val Lys
    50

<210> SEQ ID NO 6
<211> LENGTH: 50
<212> TYPE: PRT
<213> ORGANISM: Penaeus vannamei

<400> SEQUENCE: 6

Tyr Arg Gly Gly Tyr Thr Gly Pro Ile Pro Arg Pro Pro Pro Ile Gly
1               5                   10                  15

Arg Pro Pro Phe Arg Pro Val Cys Asn Ala Cys Tyr Arg Leu Ser Val
            20                  25                  30

Ser Asp Ala Arg Asn Cys Cys Ile Lys Phe Gly Ser Cys Cys His Leu
        35                  40                  45

Val Lys
    50

<210> SEQ ID NO 7
<211> LENGTH: 62
<212> TYPE: PRT
<213> ORGANISM: Penaeus vannamei

<400> SEQUENCE: 7

Glu Val Tyr Lys Gly Gly Tyr Thr Arg Pro Ile Pro Arg Pro Pro Pro
1               5                   10                  15

Phe Val Arg Pro Leu Pro Gly Gly Pro Ile Gly Pro Tyr Asn Gly Cys
            20                  25                  30

Pro Val Ser Cys Arg Gly Ile Ser Phe Ser Gln Ala Arg Ser Cys Cys
        35                  40                  45

Ser Arg Leu Gly Arg Cys Cys His Val Gly Lys Gly Tyr Ser
    50                  55                  60

<210> SEQ ID NO 8
<211> LENGTH: 21
<212> TYPE: DNA
<213> ORGANISM: Penaeus vannamei
<220> FEATURE:
<223> OTHER INFORMATION: PCR primer

<400> SEQUENCE: 8
gtgtacaagg gcggttacac g                                           21

<210> SEQ ID NO 9

```
<211> LENGTH: 21
<212> TYPE: DNA
<213> ORGANISM: Penaeus vannamei
<220> FEATURE:
<223> OTHER INFORMATION: PCR primer

<400> SEQUENCE: 9
caacaggttg tcaagcgagg t                                              21

<210> SEQ ID NO 10
<211> LENGTH: 37
<212> TYPE: DNA
<213> ORGANISM: Artificial Sequence
<220> FEATURE:
<223> OTHER INFORMATION: PCR primer

<400> SEQUENCE: 10
gcgcgcaagc ttggacaaga gatacagggg cggttac                             37

<210> SEQ ID NO 11
<211> LENGTH: 35
<212> TYPE: DNA
<213> ORGANISM: Artificial Sequence
<220> FEATURE:
<223> OTHER INFORMATION: PCR primer

<400> SEQUENCE: 11
gcgcgcggat ccttatcctt ttactaagtg acaac                               35

<210> SEQ ID NO 12
<211> LENGTH: 37
<212> TYPE: DNA
<213> ORGANISM: Artificial Sequence
<220> FEATURE:
<223> OTHER INFORMATION: PCR primer

<400> SEQUENCE: 12
gcgcgcaagc ttggacaaga gacaagtgta caagggc                             37

<210> SEQ ID NO 13
<211> LENGTH: 28
<212> TYPE: DNA
<213> ORGANISM: Artificial Sequence
<220> FEATURE:
<223> OTHER INFORMATION: PCR primer

<400> SEQUENCE: 13
gcgcgcggat cctcaaaccg gaatatcc                                       28

<210> SEQ ID NO 14
<211> LENGTH: 20
<212> TYPE: DNA
<213> ORGANISM: Artificial Sequence
<220> FEATURE:
<223> OTHER INFORMATION: RT-PCR primer for cloning penaeidin-3
<220> FEATURE:
<221> NAME/KEY: variation
<222> LOCATION: (1)..(20)
<223> OTHER INFORMATION: n at positions 3,9 and 15 = inosine, h at
      position 6 = a or c t, w at positions 7 and 13 = a or t, s at
      positions 8 and 14 = c or g, y at position 12 = c or t, r at
      position 18 = a or g.

<400> SEQUENCE: 14
ggnathwsnt tywsncargc                                                20

<210> SEQ ID NO 15
```

```
<211> LENGTH: 7
<212> TYPE: PRT
<213> ORGANISM: Artificial Sequence
<220> FEATURE:
<223> OTHER INFORMATION: Penaeidin N-terminal motif
<220> FEATURE:
<221> NAME/KEY: variation
<222> LOCATION: (1)..(7)
<223> OTHER INFORMATION: Xaa at position 2 = non-polar, neutral amino
      acid; Xaa at position 4 = basic amino acid; Xaa at position 6 =
      proline.

<400> SEQUENCE: 15

Pro Xaa Pro Xaa Pro Xaa Pro
 1               5

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence:  Penaeid
      C-terminal motif
<220> FEATURE:
<221> NAME/KEY: VARIANT
<222> LOCATION: (1)..(23)
<223> OTHER INFORMATION: Xaa = any amino acid.

<400> SEQUENCE: 16

Cys Xaa Xaa Cys Xaa Xaa Xaa Xaa Xaa Xaa Xaa Xaa Xaa Xaa Cys Cys Xaa Xaa
 1               5                  10                  15

Xaa Xaa Xaa Cys Cys
         20

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:  Penaeid
      N-terminal motif
<220> FEATURE:
<221> NAME/KEY: VARIANT
<222> LOCATION: (1)..(13)
<223> OTHER INFORMATION: Xaa at positions 2, 8 and 9 = nonpolar, neutral
      amino acid; Xaa at positions 4 and 10 = basic amino acid; Xaa at
      position 6 = proline; Xaa at positions 12 and 13 = nonpolar,
      neutral amino acid or proline.

<400> SEQUENCE: 17

Pro Xaa Pro Xaa Pro Xaa Pro Xaa Xaa Xaa Pro Xaa Xaa
 1               5                  10

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence:  Penaeid
      N-terminal motif
<220> FEATURE:
<221> NAME/KEY: VARIANT
<222> LOCATION: (1)..(18)
<223> OTHER INFORMATION: Xaa  at positions 2, 8, 9, 12, 14, 15, 17 and
      18 = nonpolar, neutral amino acid; Xaa at positions 4 and 10 =
      basic amino acid; Xaa at position 6 = proline.

<400> SEQUENCE: 18

Pro Xaa Pro Xaa Pro Xaa Pro Xaa Xaa Xaa Pro Xaa Pro Xaa Xaa Pro
 1               5                  10                  15
```

```
Xaa Xaa Pro

<210> SEQ ID NO 19
<211> LENGTH: 6
<212> TYPE: PRT
<213> ORGANISM: Artificial Sequence
<220> FEATURE:
<223> OTHER INFORMATION: Penaeidin N-terminal motif
<220> FEATURE:
<221> NAME/KEY: VARIANT
<222> LOCATION: (1)..(6)
<223> OTHER INFORMATION: Xaa at position 2 = non-polar, neutral amino
      acid; Xaa at position 4 = basic amino acid.

<400> SEQUENCE: 19

Pro Xaa Pro Xaa Pro Pro
 1               5

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence:  Penaeid
      C-terminal motif
<220> FEATURE:
<221> NAME/KEY: VARIANT
<222> LOCATION: (1)..(23)
<223> OTHER INFORMATION: Xaa = any amino acid.

<400> SEQUENCE: 20

Cys Xaa Xaa Xaa Cys Xaa Xaa Xaa Xaa Xaa Xaa Xaa Xaa Xaa Cys Cys Xaa
 1               5                   10                  15

Xaa Xaa Xaa Xaa Cys Cys
         20

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:  Penaeid
      N-terminal motif
<220> FEATURE:
<221> NAME/KEY: VARIANT
<222> LOCATION: (1)..(12)
<223> OTHER INFORMATION: Xaa at positions 2, 7 and 8 = nonpolar, neutral
      amino acid; Xaa at positions 4 and 9 = basic amino acid; Xaa at
      positions 11 and 12 = nonpolar, neutral amino acid or proline.

<400> SEQUENCE: 21

Pro Xaa Pro Xaa Pro Pro Xaa Xaa Xaa Pro Xaa Xaa
 1               5                   10

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:  Penaeid
      N-terminal motif
<220> FEATURE:
<221> NAME/KEY: VARIANT
<222> LOCATION: (1)..(18)
<223> OTHER INFORMATION: Xaa  at positions 2, 7, 8, 11, 13, 14, 16 and
      17 = nonpolar, neutral amino acid; Xaa at positions 4 and 9 =
      basic amino acid.

<400> SEQUENCE: 22

Pro Xaa Pro Xaa Pro Pro Xaa Xaa Xaa Pro Xaa Pro Xaa Xaa Pro
```

```
                   1               5              10              15

Xaa Xaa Pro

<210> SEQ ID NO 23
<211> LENGTH: 82
<212> TYPE: PRT
<213> ORGANISM: Penaeus vannamei
<220> FEATURE:
<223> OTHER INFORMATION: Penaeidin 3 isoform

<400> SEQUENCE: 23

Met Arg Leu Val Val Cys Leu Val Phe Leu Ala Ser Phe Ala Leu Val
 1               5                  10                  15

Cys Gln Gly Gln Val Tyr Lys Gly Gly Tyr Thr Arg Pro Val Pro Arg
            20                  25                  30

Pro Pro Pro Phe Val Arg Pro Leu Pro Gly Gly Pro Ile Gly Pro Tyr
        35                  40                  45

Asn Gly Cys Pro Val Ser Cys Arg Gly Ile Ser Phe Ser Gln Ala Arg
    50                  55                  60

Ser Cys Cys Ser Arg Leu Gly Arg Cys Cys His Val Gly Lys Gly Tyr
 65                  70                  75                  80

Ser Gly

<210> SEQ ID NO 24
<211> LENGTH: 81
<212> TYPE: PRT
<213> ORGANISM: Penaeus vannamei
<220> FEATURE:
<223> OTHER INFORMATION: Penaeidin 3 isoform

<400> SEQUENCE: 24

Met Arg Leu Val Val Cys Leu Val Phe Leu Ala Ser Phe Ala Leu Val
 1               5                  10                  15

Cys Gln Gly Gln Val Tyr Lys Gly Gly Tyr Thr Arg Pro Ile Pro Arg
            20                  25                  30

Pro Pro Phe Val Arg Pro Val Pro Gly Gly Pro Ile Gly Pro Tyr Asn
        35                  40                  45

Gly Cys Pro Val Ser Cys Arg Gly Ile Ser Phe Ser Gln Ala Arg Ser
    50                  55                  60

Cys Cys Ser Arg Leu Gly Arg Cys Cys His Val Gly Lys Gly Tyr Ser
 65                  70                  75                  80

Gly
```

CRUSTACEAN ANTIMICROBIAL PEPTIDES

This application is a 371 of PCT/FR98/01583, filed Jul. 20, 1998.

The invention relates to new antimicrobial peptides produced by penaeid prawns.

Peptides endowed with antimicrobial properties are produced by a wide variety of (animal or plant) species in which they participitate in nonspecific mechanisms of defence against infections. These peptides are the subject of increasing interest, in particular because they generally possess a broad activity spectrum and a low cytotoxicity for eukaryotic cells.

Comparisons of the amino acid sequences, of the secondary structures and the functional similarities have made it possible to define four main groups to which most of the antimicrobial peptides described up until now can be attached. For a review, cf. for example HOFFMANN et al., in Phylogenetic Perspectives in Immunity; The Insect Host Defense. Chapter 4, pp. 43–65 (1994):

1. A first group comprises linear peptides consisting essentially of basic and hydrophobic amino acids; the cecropins of insects and of mammals, and the magainins of the skin of batrachians, in particular are classified in this group;
2. A second group comprises peptides comprising intramolecular disulphide bridges; the defensins of insects or of mammals, the brevinins of the skin of batraciens, the thanatin of insects, which exhibits a strong sequence homology with the brevinins [FEHLBAUM et al. Proc. Natl. Acad. Sci. USA. 93, pp. 1221–1225, (1996)], the tachyplesins, produced by primitive marine arthropods, as well as various peptides obtained from the haemolymph of scorpions [EHRET-SABATIER et al., J. Biol. Chem., 271, 47, pp. 29537–29544, (1996)], in particular are classified in this group;
3. The third group comprises the peptides rich in proline, among which there may be classified the apidaecins and the abaecins of hymenopterans, drosocin and pyrrhocoricin, also produced by insects, and the bactenecins of mammals. The only antimicrobial peptide produced by a decapod crustacean which had been characterized up until now also belongs to this class: it is an antibacterial peptide rich in proline, similar to bactenecin-7, and obtained from the haemocytes of the crab Carcinus maenas [SCHNAPP et al., Eur. J. Biochem. 240, pp. 532–539 (1996)];
4. The fourth class comprises peptides or polypeptides rich in glycine, such as attacins, sarcotoxins and diptericins, all isolated from insects.

The inventors have now purified and characterized new antimicrobial peptides from the haemolymph of penaeid prawns, and have also obtained DNA sequences encoding these peptides.

The subject of the present invention is these antimicrobial peptides, called hereinafter penaeidins, which possess the following characteristics:

- their molecular mass is about 5 to 7 kDa;
- their pHi is greater than or equal to 9;
- their N-terminal sequence comprises a region (A) of about 15 to 25 amino acids, rich in proline, (at least ⅛ and preferably between ⅛ and ⅓ of the amino acids of this region are prolines);
- their C-terminal portion comprises a region (B) of about 20 to 30 amino acids, which contains 6 cysteine residues forming three intramolecular disulphide bridges.

According to a preferred embodiment of the present invention, region (A) comprises the following sequence (I):

Pro $Xaa_1$ ProXaa$_2$ ProXaa$_3$ Pro(I, SEQ ID NO: 15 or 19)

in which Pro represents a proline, $Xaa_1$, represents a nonpolar neutral amino acid, $Xaa_2$ represents a basic amino acid, $Xaa_3$ represents a proline or a peptide bond.

According to a preferred feature of this embodiment, region (A) comprises the following sequence (II):

ProXaa$_1$ ProXaa$_2$ ProXaa$_3$ ProXaa$_1$ Xaa$_1$ Xaa$_2$ ProXaa$_4$ Xaa$_4$ (II, SEQ ID NO: 17 or 21)

in which Pro, Xaa$_1$, Xaa$_2$ and Xaa$_3$ are as defined above, and Xaa4 represents a nonpolar neutral amino acid or a proline.

Advantageously, region (A) comprises the following sequence (III):

ProXaa$_1$ ProXaa$_2$ ProXaa$_3$ ProXaa$_1$ Xaa$_1$ Xaa$_2$ ProXaa$_1$ Pro Xaa$_1$ Xaa$_1$ ProXaa$_1$ Xaa$_1$ Pro(III, SEQ ID NO: 18 or 22)

in which Pro, Xaa$_1$, Xaa$_2$ and Xaa$_3$ are as defined above.

According to another preferred embodiment of the present invention, the 6 cysteine residues of region (B) are arranged according to the following sequence (IV):

Cys $S_1$ Cys $S_2$ Cys Cys $S_3$ Cys Cys (IV, SEQ ID NO: 16 or 20)

in which Cys represents a cysteine, $S_1$ represents an amino acid or a peptide sequence of 2 or 3 amino acids, $S_2$ represents a peptide sequence of 10 amino acids, $S_3$ represents a peptide sequence of 5 amino acids.

The present invention also encompasses peptides comprising or consisting of fragments of at least 5 amino acids of a penaeidin as defined above, and in particular peptides comprising or consisting of region (A) and/or region (B), as well as peptides comprising or consisting of sequences (I), (II), (III) and/or (IV).

According to a preferred embodiment of a peptide in accordance with the invention, its N-terminal end is blocked by a pyroglutamic acid residue, and/or its C-terminal end is amidated.

By way of illustration of the subject of the present invention, the characteristics of 3 penaeidins isolated from the haemolymph of the prawn Penaeus vannamei, called hereinafter penaeidin 1, penaeidin 2 and penaeidin 3, are more specifically indicated below.

"The sequences of these 3 peptides (1-letter code) are represented in FIGS. 1a (penaeidin 1, SEQ ID NO: 5), 1b (penaeidin 2, SEQ ID NO: 6 with amidated C-terminus) and 1c (penaeidin 3, SEQ ID NO: 7 with amidated C-terminus and pyroglutamic acid at the N-terminus); the alignment of the 3 sequences is represented in FIG. 1d: the conserved sequences are delimited. FIG. 2 represents a cDNA sequence of penaeidin 2 and the corresponding peptide sequence (3-letter code); FIG. 3A represents a cDNA sequence of penaeidin 3 and the corresponding peptide sequence (3-letter code); FIG. 3B represents the peptide sequence (1-letter code) of other isoforms of penaeidin 3 (P3-b and P3-c, SEQ ID NOS: 23 and 24, respectively): the sequence variations are delimited."

The cDNA sequences of penaeidin 2 and of penaeidin 3 are respectively represented in the sequence listing in the annex under the numbers SEQ ID NO: 1 and SEQ ID NO:3, and the sequences of their products of translation are respectively represented in the sequence listing in the annex under the numbers SEQ ID NO: 2 and SEQ ID NO: 4.

The peptide sequences of the mature forms of penaeidins 1, 2 and 3 are respectively represented in the sequence listing in the annex under the numbers SEQ ID NO: 5, SEQ ID NO: 6 and SEQ ID NO: 7.

These penaeidins exhibit no significant homology with the antimicrobial peptides known in the prior art, and define a new group of antimicrobial peptides.

Penaeidins 1 and 2 comprise 50 amino acids, and have a molecular mass of about 5.5 kDa; penaeidin 3 comprises 62 amino acids and its molecular mass is about 6.6 kDa.

They are cationic peptides possessing a net positive charge of 7 for penaeidins 1 and 2, and of 8 for penaeidin 3; their calculated isoelectric points vary from 9.34 for penaeidins 1 and 2, to 9.84 for penaeidin 3.

The 3 peptides have an N-terminal domain rich in proline, and a C-terminal domain comprising 6 cysteine residues forming three intramolecular disulphide bridges, and where the 4 cysteine residues closest to the C-terminal end are organized into 2 doublets separated by 5 residues.

The most central cysteines are respectively separated by 1, 2, or 3 residues in penaeidins 1, 2 and 3.

The N-terminal end of penaeidin 3 is blocked by a pyroglutamic acid residue. Blocking by similar residues has already been observed in other antimicrobial peptides.

The C-terminal end of penaeidins 2 and 3 is amidated. Such a C-terminal amidation has already been observed for certain antimicrobial peptides of other marine invertebrates (Limulus tachyplesins), as well as for the cecropins of insects and the magainins of amphibians. Such a modification reinforces the stability of the molecule, and it appears that it increases the antimicrobial activity.

Penaeidins possess a high stability and are in particular highly resistant to proteolysis. They are essentially active against Gram-positive bacteria, and also exhibit activity against Gram-negative bacteria; they possess, in addition, fungicidal properties.

Penaeidins and their fragments, as defined above, may be obtained, for example, by extraction from animals producing them, and also by peptide synthesis, or advantageously by genetic engineering, by expressing at least one nucleic acid sequence encoding a penaeidin or a fragment thereof in an appropriate host cell.

The present invention also encompasses nucleic acids comprising a segment of at least 10 bp, and preferably at least 18 bp of the gene for a penaeidin.

Nucleic acids in accordance with the invention, and in particular cDNAs for penaeidin, or portions thereof, may be obtained by screening nucleic acid libraries with the aid of oligonucleotides derived from the sequences represented in FIGS. 1, 2 or 3, or their complementary sequences.

Nucleic acids in accordance with the invention also include expression cassettes comprising at least one nucleic acid sequence encoding a penaeidin or a fragment thereof, under transcriptional control of an appropriate promoter.

"Appropriate promoter" is understood to mean any promoter which is functional in the host cell designated to harbour the expression cassette.

An expression cassette in accordance with the invention may also comprise, in addition, one or more nucleic acid sequence(s) which make it possible to enhance the secretion of the penaeidin or of its fragment by the host cell, for example a sequence encoding a signal peptide. The nucleic acid sequence encoding the signal peptide is placed at the 5' end of the nucleic acid sequence encoding the penaeidin or its fragment.

The nucleic acid sequence encoding the signal peptide may be a sequence encoding a penaeidin signal peptide, or alternatively a sequence encoding a heterologous signal peptide. A sequence will be chosen which comprises, at the C-terminal end, a site for proteolysis capable of being recognized by a signal peptidase of the host cell designated to harbour the expression cassette.

The subject of the invention is also:

recombinant vectors characterized in that they comprise at least one nucleic acid in accordance with the invention, and in particular the vectors comprising an expression cassette as defined above;

prokaryotic or eukaryotic cells transformed with an expression cassette according to the invention. They may be cells maintained in culture, or cells forming part of a pluricellular, animal or plant, organism. The expression cassette present in the transformed cell may be either incorporated into the chromosomal DNA of the said cell, or may be carried by an extra chromosomal vector.

The subject of the invention is also a method of producing a penaeidin or a fragment thereof, characterized in that it comprises the expression of the said penaeidin or of the said fragment in at least one transformed cell in accordance with the invention.

The peptides in accordance with the invention may be expressed in cultures of transformed cells using techniques similar to those used for antimicrobial peptides of the prior art, for example in insect cells, as described by HELLERS et al. [Eur. J. Biochem. 199, pp. 435–439, (1991)] for cecropins, or in yeast, as described by REICHHART et al. [Invertebrate Reproduction and Development, 21, pp. 15–24, (1992)].

They may also be expressed in transgenic plants or animals, in order to increase the resistance of the latter to infections, as described for example by JAYNES et al., [Plant Science, 89, pp. 43–53 (1993)] in the case of peptides which are analogues of cecropin B, expressed in transgenic tobacco plants, or by NORELLI et al. [Euphytica, 77, pp. 123–128 (1994)] for transgenic young apple trees expressing the gene of attacin-E.

The peptides in accordance with the invention can be used in particular for the production of products and in particular of medicaments against infections, for example antibacterials or fungicides.

Such products find their application for the prevention and the treatment of various microbial diseases, in a very wide variety of sectors, in particular in the fields of health and agriculture, and in that of aquaculture, for limiting the development of infectious diseases in breeding farms.

The present invention will be understood more clearly with the aid of the additional description which follows, which refers to examples of purification of the antimicrobial peptides in accordance with the invention, and their characterization.

EXAMPLE 1

ISOLATION OF ANTIMICROBIAL PEPTIDES FROM THE PRAWN *PENAEUS VANNAMEI*

225 ml of haemolymph were obtained from 500 prawns, by collecting samples from the central sinus, situated at the base of the first abdominal segment. The collection of sample was made in the presence of anticoagulant buffer (10% sodium citrate, pH 7, supplemented with 200 $\mu$M of phenylthiourea and 40 $\mu$g/ml of aprotinin. The haemolymph was then centrifuged at 700 g for 15 minutes at 4° C. in order to remove the blood cells. The plasma and the haemocytes are stored separately at −70° C. up to their use.

1.1 Preparation of the Fractions of the Haemolymph by Acid Extraction a) Plasma:

The plasma is diluted with demineralized water (1 volume of plasma per 1 volume of water), and 0.1% (v/v) of trifluoroacetic acid is added to this mixture. The pH was brought to 3.9 with the aid of 1 M HCl in a bath cooled with ice, with gentle stirring for 1 hour. Two successive centrifugations at 8000 g and at 4° C. were carried out in order to clarify the supernatant which is stored on ice at 4° C. up to its use.

b) Haemocytes:

Cytosol

After thawing, the haemocytes are homogenized with the aid of a DOUNCE apparatus (maximum 152 $\mu$, minimum 76 $\mu$) in 50 mM Tris buffer, pH 8.7, containing 50 mM NaCl. After centrifugation (8000 g, 20 min, 4° C.), the supernatant (cytosol fraction) is acidified to a pH of 3.6 by addition of 1 M HCl and stored at 4° C.

Organelles

The pellet containing the cellular organelles is extracted by sonication (3–30 s) at medium power in 2 M acetic acid. The debris is removed by centrifugation (8000 g, 20 min, 4° C.) and the acidic extract stored at 4° C. up to its use.

1.2 Purification of the Peptides

A) Solid phase extraction

The plasma fraction and the cytosol and organelle extracts were deposited separately on 35 cm$^3$ SEP-PAK C$_{18}$ VAC cartridges (10 g WATERS ASSOCIATES), equilibrated with acidified water (0.05% of trifluoroacetic acid).

After washing with acidified water, 3 elutions are carried out using successively 5%, 40% and 80% acetonitrile solutions in acidified water. The different fractions obtained are lyophilized and reconstituted with microfiltered water prior to purification by reversed-phase HPLC.

B) HPLC purification

1: Reversed-phase HPLC.

The fractions eluted at 5% and 40% of the SEP-PAK column were subjected to a reversed-phase chromatography on an AQUAPORE RP300 C$_8$ column (4.6×220 mm, BROWNLEE™), equilibrated in acidified water (0.05% TFA). The separation of the 5% SEP-PAK fraction is carried out with the aid of a linear gradient of 0 to 5% acetonitrile in acidified water, at a flow rate of 1 ml/min for 80 min.

For the 40% fraction, a linear gradient of 2 to 60% acetonitrile is used under the same conditions. The fractions are collected, dried under vacuum, reconstituted with the aid of ultrafiltered water, and their antimicrobial activity is tested.

2: Exclusion chromatography.

The fractions obtained at the end of the reversed-phase chromatography, exhibiting antimicrobial activity, are purified by exclusion chromatography using 2 serially linked HPLC columns (ULTRASPHEROGEL SEC 3000 column and ULTRASPHEROGEL SEC 2000 column, 7.5×300 mm, BECKMAN) protected by a precolumn (ULTRASPHEROGEL SEC, 7.5×40 mm, BECKMAN).

The elution is carried out under isocratic conditions in the presence of 30% acetonitrile in acidified water, at a flow rate of 0.5 ml/min. The fractions are collected and tested for their antimicrobial activity.

3: Reversed-phase chromatography

The peptides were purified by reversed-phase chromatography on the same column as in step 1 at a controlled temperature of 35° C.

The peptides 1 and 2 were purified with a linear biphasic gradient: of 2 to 21% acetonitrile in acidified water (0.05% TFA) over 10 min, and then of 21 to 35% acetonitrile over 50 min at a flow rate of 0.25 ml/min.

Peptide 3 was purified with the aid of a linear biphasic gradient: of 2 to 23% acetonitrile in acidified water over 10 min, and then of 23 to 37% acetonitrile over 50 min at a flow rate of 0.25 ml/min at 35° C.

4: Last purification steps

The last purification steps for the peptides were performed on DELTA PAK HPI C$_{18}$ reversed-phase column, 2×150 mm, WATERS ASSOCIATES, at a temperature of 40° C. with a flow rate of 0.25 ml/min using the biphasic gradients described above.

The elution is monitored by ultraviolet absorption at 225 nm. The fractions are collected in polypropylene tubes, concentrated under vacuum and reconstituted with water sterilized by filtration prior to the measurement of the antimicrobial activity.

EXAMPLE 2

ANTIMICROBIAL ACTIVITY OF THE FRACTIONS OBTAINED

The 40% SEP PAK fractions obtained from the plasma extract, from the organelles of the haemocytes, and from the cytosolic fraction, which are respectively designated hereinafter by the names P40, HO40 and HC40, were mainly studied. All the fractions were tested for their activity against 2 bacterial strains and against a filamentous fungus.

Microorganisms:

The microbial strains used to determine the antimicrobial activities are the following:

*Micrococcus luteus* (Gram-positive strain);

*Escherichia coli* (Gram-negaitve strain);

*Neurospora crassa* (filamentous fungus).

The bacteria are cultured with a starting optical density $A_{600}$=0.001 in "Poor-Broth" nutrient medium (1% bactotryptone, 0.5% NaCl w/v).

Antibacterial assays:

The fractions were tested by inhibition of growth in liquid phase.

10 $\mu$l aliquots of each fraction to be tested are incubated in microtitre plates with 100 $\mu$l of a suspension of bacteria at the midlogarithmic phase.

The bacterial growth is measured by determining the optical density $A_{600}$ after an incubation of 24 hours at 30° C.

An identical procedure was used to determine the minimum inhibitory concentration (MIC) of the molecules on these bacterial strains. The MIC values correspond to an interval a-b of peptide concentrations, where a represents the highest concentration at which bacterial growth is observed, and b is the lowest concentration which causes 100% inhibition of growth.

Measurement of the bacteriostatic properties

A midlogarithmic phase culture of Micrococcus luteus in the "Poor Broth" medium defined above was incubated at 30° C. in the presence of the peptide or (as control) of water. The final concentration of the molecules tested is 8 times higher than the MIC. 20-$\mu$l alquots are collected at various time intervals and cultured on nutrient agar plate. The number of colonies formed (CFU) is determined after 24 hours of incubation at 37° C.

Antifungal activity

The antifungal activity was determined against *Neurospora crassa* and *Fusarium oxysporum* by a test of inhibition of growth in liquid phase.

80 $\mu$l of fungal spores (final concentration: 10$^4$ spores/ml) are suspended in ½ Potato Dextrose Broth (DIFCO) supplemented with tetracycline (10 $\mu$g/ml) and cefotaxime (100 $\mu$g/ml). This suspension was added to 10 $\mu$l of the fraction to be tested in microtitre plates. The final volume is brought to 100 $\mu$l by addition of 10 $\mu$l of water. Growth inhibition can be observed under a microscope after 24 hours of incubation at 25° C. in the dark, and measured by the variation in the optical density at 600 nm after 48 hours.

No activity was obtained for the fractions obtained from HC40. On the other hand, as shown respectively in FIGS. 4 and 5, some of the fractions obtained from P40 and HO40 exhibit antimicrobial activity and possess a common active zone corresponding to the fractions eluted between 47 and 60 min (26 to 29% acetonitrile), where activity is observed against the 2 bacterial strains and the fungus.

Figure 5:
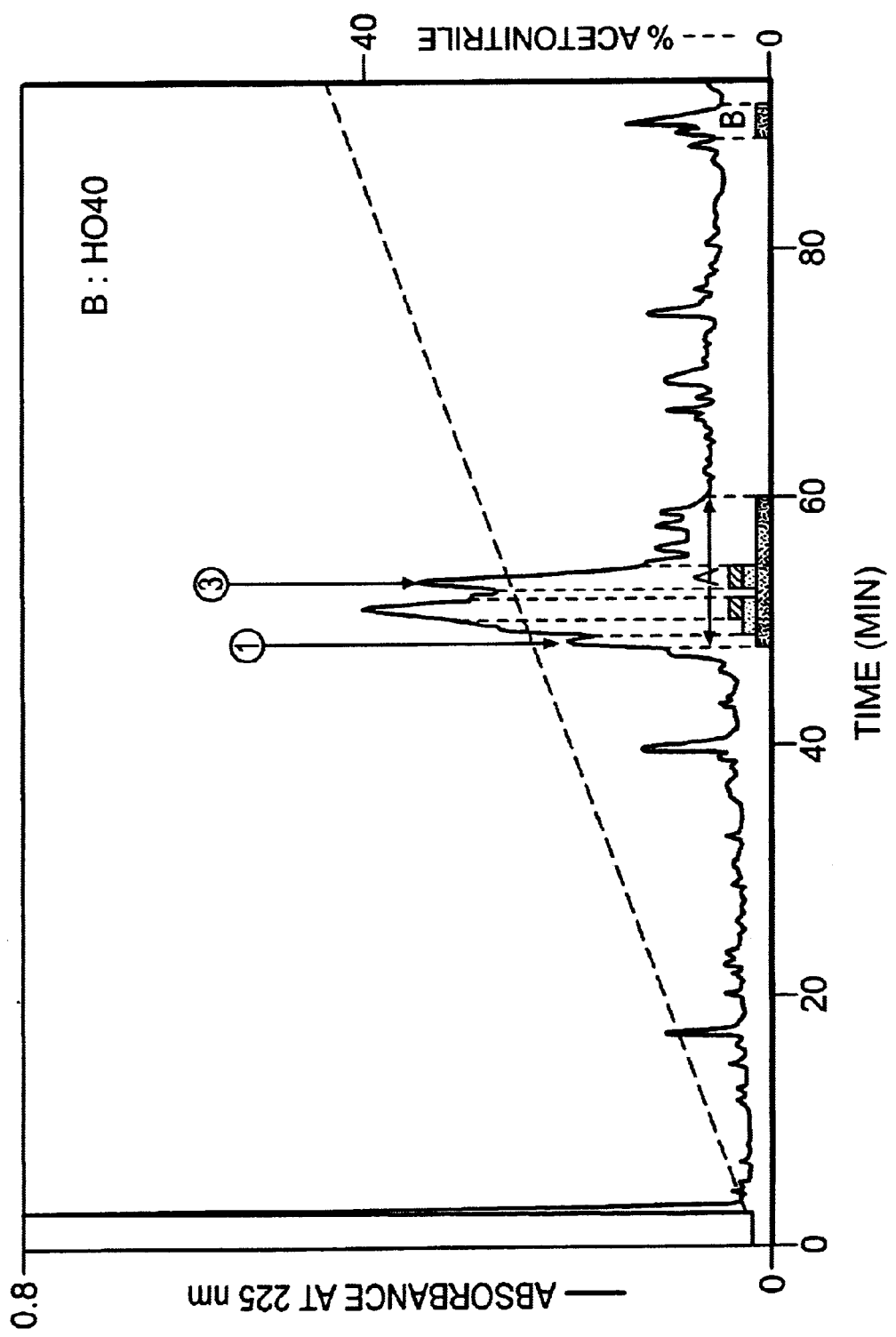

Legend to FIGS. 4 and 5:

The elution time in min is indicated on the x-axis. The absorbance at 225 nm is represented on the y-axis. The antimicrobial activity against *Escherichia coli* D31 (hashed rectangle), *Micrococcus luteus* (black rectangle) and *N. crassa* (grey rectangle) is indicated for the relevant fractions. The regions of the curve corresponding to the fractions exhibiting antimicrobial activity are indicated by the letters A, B and C. The fractions from which penaeidins 1, 2 and 3 were purified are indicated by the arrows 1, 2 and 3.

2 regions also exhibiting antimicrobial activity were obtained after reversed-phase chromatography of the plasma fraction. The P40B fractions, which are eluted at around 40 min (21–22% acetonitrile), contain molecules which are active against the 3 microorganisms tested, and P40C, corresponding to molecules eluted at around 75 min, 38–39% acetonitrile, are active only against *Micrococcus luteus*. Neither of these two zones is present in the chromatogram for HO40, in which other fractions eluted at about 90 min (45–46% acetonitrile) are active only against *Micrococcus luteus*.

EXAMPLE 3

DETERMINATION OF THE STRUCTURE OF THE PEPTIDES OBTAINED

The three peptides purified as indicated in Example 1 above were characterized by successive biochemical and molecular biology techniques.

Their molecular mass was determined by mass spectrometry; this molecular mass is respectively 5484.8 Da and 5520.0 Da for peptides P1 and P2, and 6617.4 Da for peptide P3.

It was possible to obtain the amino acid sequence of P1 by direct sequencing by Edman degradation.

P1 is a peptide of 50 residues, containing 14% of proline among the 19 N-terminal residues, and 6 cysteines forming 3 intramolecular disulphide bridges in the C-terminal domain. P1 is rich in basic amino acids, as indicated by the presence of 5 arginines and 2 lysines distributed over the entire length of the peptide.

As regards peptide P2, direct sequencing made it possible to obtain only a partial sequence of 21 N-terminal residues. This sequence differs from that of penaeidin 1 only in the replacement of leucine at position 20 in P1 with a phenylalanine in P2.

As regards peptide P3, it was not possible to establish its N-terminal sequence by the Edman degradation technique, which suggests a blocking of its N-terminal end.

S-pyridylethylation followed by mass spectrometry analysis, and the detection of the variation in mass induced by S-pyridylethylation, shows the presence of 6 cysteine residues. After enzymatic cleavage of the S-pyridylethylated peptide, the fragments obtained were purified, analysed by mass spectrometry, and by Edman degradation. The sequence of the $NH_2$-terminal end was determined by nanoES-MS (nanoElectrospray Mass Spectrometry). It was thus possible to determine that the $NH_2$-terminal residue of this peptide was cyclized into pyroglutamic acid.

EXAMPLE 4

CLONING OF THE CDNA FOR PENAEIDINS cDNA for penaeidin 3:

A probe consisting of degenerate oligonucleotides corresponding to residues 38–44 of peptide P3, and having the following sequence:

5' (GGIAT (A/T/C) (A/T) (G/C) ITT (C/T) (A/T) (G/C) ICA(A/G) GC)3' (SEQ ID NO:1) was prepared.

This probe made it possible to obtain, by reverse transcription followed by polymerase chain reaction (PCR) starting with total poly(A)$^+$ RNAs of haemocytes of adult prawns, harvested 6 and 12 hours after a bacterial challenge, an amplification product consisting of a fragment of 497 base pairs. After sequencing, this fragment was identified as a P3 cDNA fragment consisting of the end of the open reading frame and the 3' untranslated region. A subfragment of 440 base pairs, obtained by enzymatic BsaI digestion from this fragment of 497 base pairs and consisting mainly of the 3' unstranslated region, was cloned into a vector pBluescript (STRATAGENE, La Jolla, Calif.). This fragment was labelled by random priming using the READY-TO-GO DNA labelling kit (PHARMACIA BIOTECH, Uppsala, Sweden), and used to screen a cDNA library obtained from poly(A)±RNAs of adult prawns, in the ZAP-EXPRESS vector (STRATAGENE, La Jolla, Calif.).

High stringency hybridizations were carried out overnight at 65° C. in a solution of 5X Denhardt, 5X SSPE, 0.1% SDS, in the presence of 100 µg/µl of salmon sperm DNA.

161 positive clones were obtained. Among these clones, 4 were sequenced. One of them contained an open reading frame encoding a sequence of 81 amino acids (P3a) starting with a methionine codon and ending with a stop codon.

The deduced amino acid sequence of this open reading frame starts with a signal peptide of 19 residues rich in hydrophobic residues. The signal peptidase cleavage site was located after the glycine residue preceding the glutamine at position 1.

This signal peptide is directly followed, at its C-terminal end, by a peptide of 63 amino acids, starting with a glutamine residue. The deduced amino acid sequence of this mature peptide clearly confirms the partial sequences of penaeidin 3 which are obtained by direct sequencing.

Starting with the hypothesis that penaeidin 3 in mature form starts with a pyroglutamic acid resulting from the cyclization of the glutamine residue (observed by a biochemical approach), the mass calculated from the deduced amino acid sequence is 56.4 Da higher than the measured mass. This suggests that penaeidin 3 is amidated at its C-terminal end by elimination of a glycine residue (57 Da).

Among the other 3 clones sequenced, 2 slightly different deduced amino acid sequences were identified (P3b and P3c). P3b differs from P3a by the replacement of an isoleucine at position 30 in P3a by a valine in P3b, whereas p3c lacks, at position 33, a proline which is present in P3a and P3b. Finally, the leucine at position 40 in P3a and P3b is replaced by a valine in p3c.

cDNA for penaeidin 2:

In order to isolate the cDNAs for the other penaeldins, a probe corresponding to a portion of the coding sequence of penaeidin 3 in which the sequence of the product of translation is highly conserved between the 3 purified peptides, was used.

This probe was obtained by polymerase chain reaction on a p3 cDNA clone using the following primers:

upstream primer: 5'GTGTACAAGGGCGGTTACACG3' (SEQ ID NO: 8).

downstream primer: 5'CAACAGGTTGTCAAGC-GAGGT3' (SEQ ID NO: 9).

The hybridization is performed under the same conditions as those described above, but at a lower hybridization temperature (50° C.) in order to ensure a lower stringency.

The clones obtained under these conditions were analysed on the basis of their restriction profile. For one of these clones, this profile was different from that observed for P3a. This clone was sequenced. The amino acid sequence deduced from the DNA sequence possesses a very high percentage identity with penaeidin 1, in particular a COOH-terminal domain which is completely identical to that established by direct sequencing of penaeidin 1. However, the presence of a phenylalanine residue at position 20 in the mature peptide, as well as the value of the molecular mass, is in favour of the cDNA for penaeidin 2. The deduced amino acid sequence comprises an additional amino acid (glycine at the C-terminal end), compared with that obtained by direct sequencing, which suggests that this glycine residue may be removed by amidation. This was confirmed by the calculation of the mass (5575.6 Da) which is 55.6 Da higher than the mass measured for penaeidin 2, whereas the calculated mass of the amidated peptide corresponds to that of penaeidin 2 measured by mass spectrometry.

It appears, in addition, that penaeidin 2 is derived from a precursor molecule possessing a "pre" region of 21 residues, which is identical to that of the signal peptide of penaeidin 3, with two additional residues (Glu-Ala) immediately preceding the observed cleavage site. Another potential cleavage site was located at position -3 upstream of the Tyr-1 residue. This other site corresponds to that which is observed in the maturation of penaeidin 3.

EXAMPLE 5

ANTIMICROBIAL ACTIVITY OF THE PURIFIED PENAEIDIN 3

The activity of the purified penaeidin 3 was tested as described in Example 2, against *Micrococcus luteus*, *Escherichia coli* D31, *Neurospora crassa* and also against *Fusarium oxysporum* which is a pathogenic fungus for penaeid prawns.

This peptide has a marked activity against *Micrococcus luteus* (MIC=0.6 to 2.5 µM) and moderate activity on *Escherichia coli* (MIC>5 µM). Penaeidin 3 is also active against the 2 fungi tested (MIC>5 µM).

When the incubation of penaeidin 3 with *Micrococcus luteus* is carried out at a concentration of 18 µM, that is to say 8 times higher than the MIC, no bacterial growth is observed after an incubation of 24 hours. Furthermore, the number of colonies formed remains constant during the different sample collections, which suggests that this molecule has a bacteriostatic effect. These results are illustrated by Table I below.

TABLE I

| Incubation time | Control | Penaeidin 3 |
|---|---|---|
| | $10^4$ cfu/ml | |
| 1 min | 3.85 | 4.30 |
| 30 min | 4.40 | 4.45 |
| 2 h | 6.70 | 3.15 |

TABLE I-continued

| Incubation time | Control | Penaeidin 3 |
|---|---|---|
| 4 h | 9.45 | 4.60 |
| 7 h | 51.50 | 4.50 |
| 24 h | >1,000 | 5.60 |

EXAMPLE 6

PRODUCTION OF RECOMBINANT PENAEIDINS

The DNA fragments encoding penaeidins-2 or -3, flanked at their amino-terminal end, were obtained by PCR using the following primers, which make it possible to insert, upstream of the sequence encoding the penaeidin, a sequence encoding the last five residues of the proregion of the yeast sex factor MFα1 and a HindIII site, and downstream of the sequence encoding the penaeidin, a BamHI site.

Primers used for penaeidin-2:

```
P2-SENSE:
  5·GCGCGCAAGCTTGGACAAGAGATACAGGGGCGGTTAC3·
         Hind III
P2-ANTI:
  5·GCGCGCGGATCCTTATCCTTTTACTAAGTGACAAC3·
         Bam HI
```

These 2 primers are respectively represented in the sequence listing under the numbers SEQ ID NO: 10 and SEQ ID NO: 11.

Primers used for penaeidin-3:

```
P3-SENSE:
  5·GCGCGCAAGCTTGGACAAGAGACAAGTGTACAAGGGC3·
         Hind III
P3-ANTI:
  5·GCGCGCGGATCCTCAAACCGGAATATCC3·
         Bam HI
```

These 2 primers are respectively represented in the sequence listing under the numbers SEQ ID NO: 12 and SEQ ID NO: 13.

The enzyme used for the PCR is Vent polymerase (NEW ENGLAND BIOLABS) which generates blunt ends. The fragments obtained were cloned between the HindIII and BamHI sites of the multisite linker of the plasmid pCR-SCRIPT (STRATAGENE).

The inserts of the plasmids thus obtained were excised with BamII and HindIII, and subcloned into the yeast expression cassette of the vector pJV1. The vector pJV1 was provided by the laboratory of Prof. HOFFMANN at Strasbourg: it is a plasmid derived from pBLUESCRIPT II into which there have been introduced the promoter of the yeast sex factor MFα1 and the preprosequence of this same factor, in which sequence there has been created, by silent mutation, a HindIII restriction site allowing the fusion in phase of the coding sequences.

The complete cassettes (about 1.4 kb) were excised from pJV1 by double SphI-BamHI digestion (partial SphI digestion for penaeidin-2) and subcloned into the shuttle vector pTG4812 [MICHAUD et al. FEBS Lett., 395: 6–10 (1996)].

The two expression vectors thus obtained are called pen2-pTG4812 and pen3-pTG4812, and allow respectively the expression of penaeidin 2 and that of penaeidin 3 in yeast.

For the production of recombinant penaeidins, the *Saccharomyces cerevisiae* TGY48-1 strain, described by REICHHART et al. [Invert. Reprod. Dev. 21(1): 15–24 (1992)], was used. It carries a ura3-Δ5 mutation which allows the selection of recombinant clones on uracil-free selective medium.

This strain was transformed with the recombinant plasmids pen2-pTG4812 and pen3-pTG4812 according to the lithium acetate method described by GIETZ et al. [Nucl. Ac. Res. 20(6): 1425 (1992)]. The recombinant yeast clones were selected on uracil-free selective medium "YNBG-casamino acids" and cultured. The recombinant penaeidins are secreted into the culture medium and are purified from the culture supernatant according to a protocol similar to that described in Example 1 above.

What is claimed is:

1. A purified antimicrobial peptide obtained from penaeid prawns with a molecular mass of about 5 to 7 kDa and an isoelectric pH greater than or equal to 9; said peptide comprising:

a) a N-terminal region (A) of about 15 to 25 amino acids, which comprises the following motif (I):
  ProXaa$_1$ ProXaa$_2$ ProXaa$_3$ Pro(SEQ ID NO:15 or 19)
  in which Xaa$_1$ is a nonpolar neutral amino acid, Xaa$_2$ is a basic amino acid and Xaa$_3$ is a proline or a peptide bond; and b) a C-terminal region (B) of about 20 to 30 amino acids, which contains 6 cysteine residues forming three intramolecular disulfide bridges and arranged according to the following motif (IV):
  Cys S$_1$ Cys S$_2$ Cys Cys S$_3$ Cys Cys (SEQ ID NO: 16 or 20)

in which S$_1$ is an amino acid or a peptide sequence of 2 or 3 amino acids, S$_2$ is a peptide sequence of 10 amino acids, and S$_3$ is a peptide sequence of 5 amino acids.

2. The peptide according to claim 1, in which region (A) comprises the following sequence (II):
ProXaa$_1$ ProXaa$_2$ ProXaa$_3$ ProXaa$_1$ Xaa$_1$ Xaa$_2$ ProXaa$_4$ Xaa$_4$ (SEQ ID NO:17 or 21)
in which Xaa$_1$, Xaa$_2$, and Xaa$_3$ are as defined in claim 1, and Xaa4 is a nonpolar neutral amino acid or a proline.

3. The peptide according to claim 1, in which region (A) comprises the following sequence (III):
ProXaa$_1$ ProXaa$_2$ ProXaa$_3$ ProXaa$_1$ Xaa$_1$ Xaa$_2$ ProXaa$_1$ ProXaa$_1$ Xaa$_1$ ProXaa$_1$ Xaa$_1$ Pro (SEQ ID NO: 18 or 22)
in which Xaa$_1$, Xaa$_2$, and Xaa$_3$ are as defined in claim 1.

4. The peptide according to claim 1, selected from the group consisting of:

the peptide having the sequence of SEQ ID NO: 5, the peptide having the sequence of SEQ ID NO: 6, and the peptide having the sequence of SEQ ID NO: 7.

5. The peptide according to claim 1, in which the N-terminal end is blocked by a pyroglutamic acid residue.

6. A method of producing an antimicrobial peptide obtained from penaeid prawns with a molecular mass of about 5 to 7 kDa and an isoelectric pH greater than or equal to 9, wherein the peptide comprises:
   a) a N-terminal region (A) of about 15 to 25 amino acids, which comprises the following motif (I):
   Pro $Xaa_1$ Pro $Xaa_2$ Pro $Xaa_3$ Pro (SEQ ID NO:15 or 19), in which $Xaa_1$ is a nonpolar neutral amino acid, $Xaa_2$ is a basic amino acid and $Xaa_3$ is a proline or a peptide bond; and
   b) a C-terminal region (B) of about 20 to 30 amino acids, which contains 6 cysteine residues forming three intramolecular disulfide bridges and which comprises the following motif (IV):
   Cys $S_1$ Cys $S_2$ Cys Cys $S_3$ Cys Cys (SEQ ID NO: 16 or 20), in which $S_1$ is an amino acid or a peptide sequence of 2 or 3 amino acids, $S_2$ is a peptide sequence of 10 amino acids and $S_3$ is a peptide sequence of 5 amino acids, the method comprising:
   expressing a nucleic acid sequence encoding the peptide in a host cell transformed with a recombinant vector containing the nucleic sequence under the transcriptional control of an appropriate promoter, wherein the peptide is expressed in the host cell.

7. The method of claim 6, further comprising recovering the peptide from the host cell.

8. The method of claim 6, wherein the nucleic acid sequence encoding the peptide is obtained by screening a nucleic acid library from a penaeid prawn with at least one oligonucleotide, or the complement thereof, of at least 20 contiguous base pairs obtained from a sequence encoding a peptide selected from the group consisting of SEQ ID NO: 5, SEQ ID NO: 6 and SEQ ID NO: 7.

9. The peptide according to claim 1, in which the C-terminal end is amidated.

* * * * *